United States Patent
Agrawal

(10) Patent No.: US 11,412,933 B2
(45) Date of Patent: Aug. 16, 2022

(54) SYSTEM FOR ANALYSING AN ACTIVITY OF BRAIN USING MAGNETIC RESONANCE IMAGING (MRI) DATA

(71) Applicant: BRAINSIGHT TECHNOLOGY PRIVATE LIMITED, Bangalore (IN)

(72) Inventor: Rimjhim Agrawal, Bangalore (IN)

(73) Assignee: BRAINSIGHT TECHNOLOGY PRIVATE LIMITED, Bangalore (IN)

( * ) Notice: Subject to any disclaimer, the term of this patent is extended or adjusted under 35 U.S.C. 154(b) by 214 days.

(21) Appl. No.: 16/932,778

(22) Filed: Jul. 19, 2020

(65) Prior Publication Data
US 2021/0015366 A1   Jan. 21, 2021

(51) Int. Cl.
| | | |
|---|---|---|
| A61B 5/00 | (2006.01) | |
| A61B 5/055 | (2006.01) | |
| A61B 5/16 | (2006.01) | |
| G06T 11/00 | (2006.01) | |
| G06T 7/33 | (2017.01) | |
| G06T 7/00 | (2017.01) | |

(52) U.S. Cl.
CPC ............ *A61B 5/0042* (2013.01); *A61B 5/055* (2013.01); *A61B 5/16* (2013.01); *A61B 5/4064* (2013.01); *A61B 5/7264* (2013.01); *G06T 7/0012* (2013.01); *G06T 7/344* (2017.01); *G06T 11/008* (2013.01); *A61B 2576/026* (2013.01); *G06T 2207/10088* (2013.01); *G06T 2207/20081* (2013.01); *G06T 2207/20084* (2013.01); *G06T 2207/30016* (2013.01)

(58) Field of Classification Search
CPC ... A61B 5/4064; A61B 5/0042; A61B 5/7264; A61B 5/16; A61B 5/055; A61B 5/165; A61B 2576/026; A61B 5/4088; G06T 7/344; G06T 7/0012; G06T 11/008; G06T 2207/30016; G06T 2207/10088; G06T 2207/20084; G06T 2207/20081
See application file for complete search history.

(56) References Cited

U.S. PATENT DOCUMENTS

| | | | |
|---|---|---|---|
| 2014/0155730 A1* | 6/2014 | Bansal | A61B 5/7282 600/407 |
| 2015/0272461 A1* | 10/2015 | Morimoto | A61B 5/7246 600/410 |
| 2021/0034912 A1* | 2/2021 | Lisi | G06T 7/0012 |
| 2021/0319899 A1* | 10/2021 | Liu | A61B 5/0042 |
| 2021/0353205 A1* | 11/2021 | Fogel | G16H 50/20 |

* cited by examiner

*Primary Examiner* — Brenda C Bernardi

(57) ABSTRACT

A system for classifying an activity and connectivity of a brain into at least one neuropsychiatric disorder from magnetic resonance imaging (MRI) images. The system includes an imaging device, a network, and a brain activity analyzing server. The system (i) generate a three-dimensional (3D) structural MRI image and a 4D functional MRI images of the brain, (ii) extracts one or more features associated with one or more regions of the brain using a parcellation scheme, (iii) analyses, using a machine learning model, an intensity of at least one voxel in the one or more regions, and (iv) classifies the activity and the connectivity of the brain into at least one neuro-psychiatric disorder based on a percentage of variation of intensity of the at least one voxel in the one or more regions of the brain over the one or more features from a predefined threshold value.

20 Claims, 11 Drawing Sheets

SYSTEM FOR ANALYSING AN ACTIVITY OF BRAIN USING MAGNETIC RESONANCE IMAGING (MRI) DATA

CROSS-REFERENCE TO RELATED APPLICATIONS

This patent application claims priority to Indian provisional patent application no: 201941029308 filed on July 19, 2019, the complete disclosures of which, in their entirety, are hereby incorporated by reference.

Technical Field

The embodiments herein generally relate to classifying brain activity based on data analysis, more particularly, a system and method for classifying neuro-psychiatric conditions based on real-time magnetic resonance images (MRI) of a brain using machine learning.

Description of the Related Art

With the economic, health, development of medical standards, the average life expectancy has been increasing. At the same time, the incidence of mental illness is growing year by year due to the increased competitive pressure and many other social factors, which becomes one of the leading causes of death. Clinically, magnetic resonance imaging (MRI), a non-invasive imaging technique, may be used to diagnose the mental illness. MRI greatly extends the understanding of the complex pathogenesis of the mental illness and changing clinical and biological features associated with the mental illness. Hence, the magnetic resonance imaging technique has become an indispensable tool in cognitive science, neuroscience, and neuro-psychiatric researches.

Existing approaches uses algorithms for determining brain activity. The existing algorithms uses fixed and predefined templates for brain zoning. The existing method may use an input feature vector predictive model for calculating predictive performance of part of the plurality regions of interest of a brain, which limits the search for one or more features of the MRI images accurately. The predictive performance of brain plays a key role to obtain the predetermined template of brain zoning composed. Existing approach has used more conventional single data type or a single feature selection technique for determining brain activity, however, it is not effectively extended to multiple modalities. Also, the predictive performance of part of the plurality regions of interest of a brain and the like of different target metric uncertain factor, limits in the promotion of various types of disease diagnosis and imaging modalities, studies for complex diseases, and poor repeatability. Existing approaches are used for detecting complex networks in magnetic response image data. The detection of complex networks may increase the complexity of analysis. Further, existing approaches uses denoising techniques before feature selection for MRI images, thereby consuming more power consumption.

Therefore, there arises a need to address the aforementioned technical drawbacks in existing technologies to analyze and classify the brain activity.

SUMMARY

In view of foregoing an embodiment herein provides a processor-implemented method for classifying an activity and connectivity of a brain into at least one neuropsychiatric disorder from magnetic resonance imaging (MRI) images. The method includes (i) obtaining one or more two-dimensional slices of structural MRI images and one or more two-dimensional slices of functional MRI images of the brain, (ii) generating a three-dimensional structural MRI image and a four-dimensional functional MRI image of the brain from the one or more two-dimensional slices of structural MRI images and the one or more two-dimensional slices of functional MRI images of the brain, (iii) extracting one or more features associated with one or more regions of the brain in a co-registered MRI image of the brain, (iv) analysing, using a machine learning model, an intensity of at least one voxel in the one or more regions of the brain over a plurality of features to determine an activity and a connectivity of the brain over the one or more features, and (v) classifying the activity and the connectivity of the brain into at least one neuropsychiatric disorder based on a percentage of variation of the intensity of the at least one voxel over the one or more features from a predefined threshold value. In some embodiments, the co-registered MRI image is created by co-registering the three-dimensional structural MRI image to the four-dimensional functional MRI image. In some embodiments, the co-registered MRI image is parcellated into the one or more regions of the brain using a parcellation scheme.

In some embodiments, the one or more regions of the brain includes at least one of an inferior frontal gyrus, a pars triangularis, a caudate, a superior temporal gyrus, a middle occipital gyrus, a parahippocampal, an anugular gyrus, a middle frontal gyrus, a supramarginal gyrus, an inferior temporal gyrus, a crus I of cerebellar hemisphere, a precentral gyrus, a precuneus, or a middle frontal gyrus.

In some embodiments, the one or more features of the brain includes at least one of a regional homogeneity, one or more derivatives of functional connectivity pearson correlation, a functional connectivity partial co-relation, a functional connectivity precision, an amplitude of low frequency fluctuation (ALFF), and a fractional Amplitude of Low Frequency Fluctuations (fALFF).

In some embodiments, the method includes calculating the functional connectivity between the one or more regions of the brain using an intensity of the at least one voxel and one or more activation time series components of the at least one voxel.

In some embodiments, the method includes calculating the amplitude of low frequency fluctuation (ALFF), and the fractional Amplitude of Low Frequency Fluctuations (fALFF) in the form of nifty file intensity maps using a bandpass filter.

In some embodiments, the method includes generating a report that visualizes percentage of deviation of the activity and the connectivity of the brain over the one or more features from the normal activity and connectivity of the brain. In some embodiments, the report includes at least one of one or more accuracy matrices, one or more percentage matching graphs, or one or more scatter plots.

In some embodiments, the method includes analysing of the intensity of the at least one voxel in the one or more regions of the brain over the one or more features by, (i) reducing the one or more features based on an importance and a contribution of the one or more features of the brain to analyse the one or more regions of the brain, (ii) analysing, using the machine learning model, on a single stack of the at least one voxel, the single stack includes any six of the extracted one or more features of the brain, and (iii) analysing, using the machine learning model, on a multi stack of the at least one voxel to obtain classification of the activity and the connectivity of the brain, the multi stack comprises 84 stacks of the at least one voxel.

In some embodiments, the machine learning model includes supervised learning algorithms and unsupervised learning algorithms. In some embodiments, the supervised learning algorithms include at least one of a decision tree learning algorithm, a linear model analysis algorithm, a support vector machine learning algorithm, graphical models, deep neural networks, or an ensemble learning algorithm.

In some embodiments, the unsupervised learning algorithms include at least one of a clustering model, a graph algorithm model, a component-based model, a hierarchical clustering algorithm, or a mixture model learning.

In some embodiments, the method includes pre-processing the two-dimensional structural MRI image slices of the brain and the two dimensional functional MRI image slices overtime of the brain for feature extraction.

In one aspect, the present disclosure provides one or more non-transitory computer readable storage medium for storing the one or more sequence of instructions, which when executed by a processor, further causes a method for classifying an activity and connectivity of a brain into at least one neuro-psychiatric disorder from magnetic resonance imaging (MRI) images. The method includes, (i) obtaining one or more two-dimensional slices of structural MRI images and one or more two-dimensional slices of functional MRI images of the brain, (ii) generating a three-dimensional structural MRI image and a four-dimensional functional MRI image of the brain from the one or more two-dimensional slices of structural MRI images and the one or more two-dimensional slices of functional MRI images of the brain, (iii) extracting one or more features associated with one or more regions of the brain in a co-registered MRI image of the brain, (iv) analysing, using a machine learning model, an intensity of at least one voxel in the one or more regions of the brain over one or more features to determine an activity and a connectivity of the brain over the one or more features, and (v) classifying the activity and the connectivity of the brain into at least one neuropsychiatric disorder based on a percentage of variation of the intensity of the at least one voxel over the one or more features from a predefined threshold value. In some embodiments, the co-registered MRI image is created by co-registering the three-dimensional structural MRI image to the four-dimensional functional MRI image. In some embodiments, the co-registered MRI image is parcellated into the one or more regions of the brain using a parcellation scheme.

In another aspect, the present disclosure provides a system for classifying an activity and connectivity of a brain into at least one neuro-psychiatric disorder from magnetic resonance imaging (MRI) images. The system includes a processor and a memory that stores a set of instructions that are executed by the processor to perform one or more functions of the system. The processor performs (i) obtaining one or more two-dimensional slices of structural MRI images and one or more two-dimensional slices of functional MRI images of the brain, (ii) generating a three-dimensional structural MRI image and a four-dimensional functional MRI image of the brain from the one or more two-dimensional slices of structural MRI images and the one or more two-dimensional slices of functional MRI images of the brain, (iii) extracting one or more features associated with one or more regions of the brain in a co-registered MRI image of the brain, (iv) analysing, using a machine learning model, an intensity of at least one voxel in the one or more regions of the brain over one or more features to determine an activity and a connectivity of the brain over the one or more features, and (v) classifying the activity and the connectivity of the brain into at least one neuropsychiatric disorder based on a percentage of variation of the intensity of the at least one voxel over the one or more features from a predefined threshold value. In some embodiments, the co-registered MRI image is created by co-registering the three-dimensional structural MRI image to the four-dimensional functional MRI image. In some embodiments, the co-registered MRI image is parcellated into the one or more regions of the brain using a parcellation scheme.

In some embodiments, the processor performs analysis of the intensity of the at least one voxel in the one or more regions of the brain over the one or more features by, (i) reducing the one or more features based on an importance and a contribution of the one or more features of the brain to analyse the one or more regions of the brain, (ii) analysing, using the machine learning model, on a single stack of the at least one voxel, the single stack comprises any six of the extracted one or more features of the brain, and (iii) analysing, using the machine learning model, on a multi stack of the at least one voxel to obtain classification of the activity and the connectivity of the brain, the multi stack comprises 84 stacks of the at least one voxel.

In some embodiments, the processor performs pre-processing the two-dimensional structural MRI image slices of the brain and the two dimensional functional MRI image slices overtime of the brain for feature extraction.

In some embodiments, the machine learning model includes supervised learning algorithms and unsupervised learning algorithms. In some embodiments, the supervised learning algorithms include at least one of a decision tree learning, a linear model analysis algorithm, a support vector machine algorithm, graphical models, deep neural networks, or an ensemble learning algorithm.

In some embodiments, the unsupervised learning algorithms include at least one of a clustering model, a graph algorithm model, a component-based model, a hierarchical clustering algorithm, or a mixture model learning.

In some embodiments, one or more regions of the brain include at least one of an inferior frontal gyrus, a pars triangularis, a caudate, a superior temporal gyrus, a middle occipital gyrus, a parahippocampal, an anugular gyrus, a middle frontal gyrus, a supramarginal gyrus, an inferior temporal gyrus, a crus I of cerebellar hemisphere, a precentral gyrus, a precuneus, or a middle frontal gyrus.

In some embodiments, one or more features of the brain include at least one of a regional homogeneity, one or more derivatives of functional connectivity pearson correlation, a functional connectivity partial co-relation, a functional connectivity precision, an amplitude of low frequency fluctuation (ALFF), or a fractional Amplitude of Low Frequency Fluctuations (fALFF).

In some embodiments, the processor calculates the functional connectivity between the one or more regions of the brain using an intensity of the at least one voxel and one or more of activation time series components of the at least one voxel.

In some embodiments, the processor calculates the amplitude of low frequency fluctuation (ALFF), and the fractional Amplitude of Low Frequency Fluctuations (fALFF) in the form of nifty file intensity maps using a bandpass filter.

BRIEF DESCRIPTION OF THE DRAWINGS

The embodiments herein will be better understood from the following detailed description with reference to the drawings, in which.

DETAILED DESCRIPTION OF THE DRAWINGS

Figure 1:
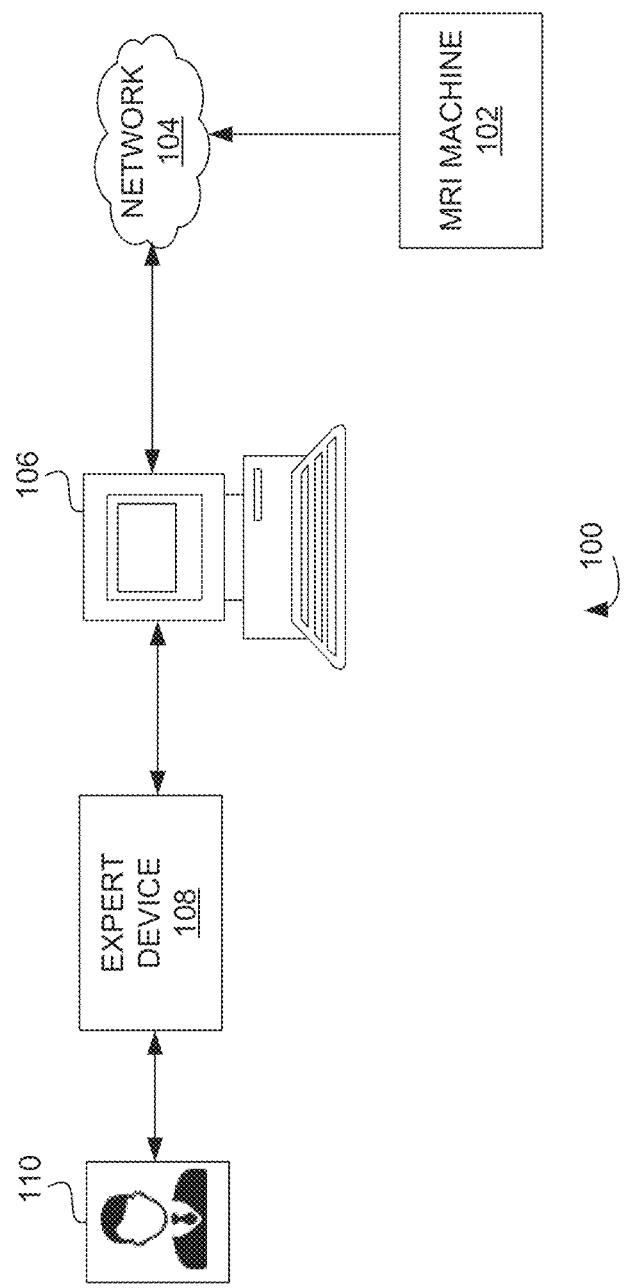
FIG. 1 illustrates a system view of a brain activity classifying system, according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for mitigating and/or overcoming drawbacks associated with current systems and methods. Referring now to the drawings, and more particularly to FIGS. 1 through 7, where similar reference characters denote corresponding features consistently throughout the figures, preferred embodiments are shown.

FIG. 1 illustrates a system view of a brain activity classifying system 100, according to an embodiment herein. The system view 100 includes an imaging device 102, a network 104, a brain activity analyzing server 106, and an expert device 108 associated with an expert 110. In some embodiments, the imaging device 102 is a Magnetic Resonance Imaging device (MRI). The imaging device 102 generates functional Magnetic Resonance Imaging (MRI) images and structural MRI images of the brain of a person. In some embodiments, the imaging device 102, may generate MRI scan of a person, for example, in a video. The brain activity analyzing server 106 includes a processor and a memory that stores a set of instructions that are executed by the processor for performing one or more functions of the brain activity analyzing server 106. The brain activity analyzing server 106 obtains the functional and structural MRI images of the brain from the imaging device 102 through the network 104 and stores the functional and structural MRI images in the memory. In some embodiments, the brain activity analyzing server 106 obtains the functional and structural MRI images of the brain from a Compact Disc Read-Only Memory (CDROM) or Digital Versatile/Video Disc (DVD). In some embodiments, the functional and structural MRI images of the brain may be downloaded from a web-based system or an application that makes the MRI images available for processing, in accordance with the methods disclosed herein. In some embodiments, the functional and structural MRI images of the brain may be received from a mobile application that may available in a handheld device. In some embodiment, the handheld device includes but not limited to, a cell phone, a handheld computing device, an electronic notepad, a smart phone and a personal assistant device. In some embodiments, the functional and structural MRI images of the brain may be received directly from a memory or storage device of the imaging device 102. In some embodiments, the network 104 includes, but not limited to, a wireless network, a wired network, a combination of the wired network and the wireless network or Internet and the like. The brain activity analyzing server 106 classifies the activity and the connectivity of the brain into at least one neuropsychiatric disorder by analyzing the MRI images of the brain. The expert device 108 is communicatively connected to the brain activity analyzing server 106 for monitoring the classification of the activity of the brain. In some embodiments, the expert device 108 includes, but not limited to, a handheld device, a mobile phone, a kindle, a Personal Digital Assistant (PDA), a tablet, a laptop, a music player, a computer, an electronic notebook or a smartphone and the like.

The brain activity analyzing server 106 obtains one or more two-dimensional slices of structural MRI images and one or more two-dimensional (2D) slices of functional MRI images of the brain from the imaging device 102. In some embodiments, the brain activity analyzing server 106 pre-processes the one or more 2D slices of structural MRI images of the brain and the one or more 2D slices of the functional MRI images overtime of the brain. In some embodiments, the pre-processing of one or more 2D slices of structural MRI image of the brain, and the 2D slices of the functional MRI image includes (i) setting an origin of the one or more 2D slices of structural MRI images of the brain, and the one or more 2D slices of the functional MRI images of the brain based on an anterior commissure, and a posterior commisure lines, (ii) calculating resting state functional MRI metrics in a native space, (iii) removing the first 10 time points for scanner calibration, wherein the time point is the total time taken for a complete scan, (iv) correcting slice time by examining time shift by small amount for each voxel sampled across slices of the one or more 2D slices of structural MRI images of the brain, and the one or more 2D slices of the functional MRI images by interpolating between the time points of sampling to give the time course that is like having sampled each voxel at the same time, (v) realigning the one or more 2D slices of structural MRI images of the brain, and the one or more 2D slices of the functional MRI images to remove movement artefacts, and (vi) generating automasks in skull stripping of the one or more 2D slices of structural MRI images of the brain, and the one or more 2D slices of the functional MRI images. The brain activity analyzing server 106 generates a three-dimensional (3D) structural MRI image of the brain and a four-dimensional (4D) functional MRI image of the brain. In some embodiments, the one or more 2D slices of structural MRI image of the brain, and the one or more 2D slices of the functional MRI image are stored in dicom format. In some embodiments, the imaging device 102 may collect data of the person in the dicom format. In some embodiments, the brain activity analyzing server 106 may use the data of the person in the dicom format, for example, the data of the person include a number of attributes, for example, a name of the person, ID of the person, etc., a number of slices of the MRI images, a voxel size, a number of functional MRI time-series points from a dicom header for image processing. In some embodiments, the brain activity analyzing server 106 stacks the data in the dicom format to generate the 3D structural MRI image and the 4D functional MRI image of the brain using an image processing technique. In some embodiments, the brain activity analyzing server 106 segments the 3D structural MRI image and the 4D functional MRI image of the brain into one or more parts. In some embodiments, for example, the brain activity analyzing server 106 segments the 4D functional MRI image of the brain into gray matter, white matter, and cerebrospinal fluid. In some embodiments, the brain activity analyzing server 106 regularizes the 3D structural MRI image and the 4D functional MRI image of the brain by penalizing excessive stretching or shrinking. In some embodiments, the brain activity analyzing server 106 regresses out motion parameters and corrects the effects of motion by removing motion-related components from the 3D structural MRI image and the 4D functional MRI image of the brain by the inclusion of calculated motion parameters. In some embodiments, the brain activity analyzing server 106 normalizes the motion artefact regressed 3D structural MRI image and 4D functional MRI image of the brain. In some embodiments, the brain activity analyzing server 106 smoothens the normalized 3D structural MRI image and 4D functional MRI image of the brain. In some embodiments, the brain activity analyzing server 106 generates a default mask for the smoothened, normalized 3D structural MRI image and 4D functional MRI image of the brain. In some embodiments, the brain activity analyzing server 106 filters higher frequency components in the 3D structural MRI image and the 4D functional MRI image of the brain to obtain low frequency components using a bandpass filter. The brain activity analyzing server 106 extracts one or more features associated with one or more regions of the brain in a co-registered MRI image of the brain. In some embodiments, the co-registered MRI image is created by co-registering the 3D structural MRI image to the 4D functional MRI image using an image processing technique. In some embodiments, the co-registered MRI image is parcellated into the one or more regions of the brain using a parcellation scheme. In some embodiments, the one or more features of the brain includes, but not limited to, one or more derivatives of functional connectivity pearson correlation, a functional connectivity partial co-relation, a functional connectivity precision, an amplitude of low frequency fluctuation (ALFF), a fractional Amplitude of Low Frequency Fluctuations (fALFF), and a regional homogeneity. In some embodiments, the amplitude of low frequency fluctuation (ALFF), and the fractional Amplitude of Low Frequency Fluctuations (fALFF) are obtained in the form of nifty file intensity maps using the bandpass filter. In some embodiments, the brain activity analyzing server 106 extracts voxel intensities over a pre-specified parcellation volume over six different features. In some embodiments, the one or more regions of the brain refer to one or more regions of interest (ROI) of the brain. In some embodiments, the brain activity analyzing server 106 parcellates the one or more ROIs of the brain using a parcellations scheme or 14 atlases map with different granularity. In some embodiments, the one or more ROIs include, but not limited to, 14 ROIs. The brain activity analyzing server 106 analyses, using a machine learning model, an intensity of at least one voxel in the one or more regions of the brain over one or more features to determine an activity and a connectivity of the brain over the one or more features. In some embodiments, the brain activity analyzing server 106 reduces the one or more features by checking the importance of the one or more features of the brain and contribution of the one or more features of the brain to analyse the one or more regions of the brain. In some embodiments, the one or more features of the brain are extracted using a standardized parcellations algorithm. In some embodiments, the brain activity analyzing server 106 applies a machine learning model on a single stack of at least one voxel. In some embodiments, the single stack includes any six of the extracted one or more features of the brain. In some embodiments, the machine learning model includes supervised learning algorithms and unsupervised learning algorithms. In some embodiments, the supervised learning algorithms include a decision tree learning, a linear model analysis, a support vector machine, graphical models, deep neural networks, an ensemble learning, classification models, and regression models. In some embodiments, the unsupervised learning algorithms include a clustering based algorithm, a graph based algorithm, and a component-based learning algorithm, a hierarchical clustering based algorithm, and a mixture model. In some embodiments, the semi-supervised and reinforcement models are applied to the single stack of the at least one voxel. In some embodiments, the brain activity analyzing server 106 applies the machine learning model on a multi-stack of the at least one voxel to obtain a classification of the activity and the connectivity of the brain into at least one neuropsychiatric disorder. In some embodiments, the multi-stack includes 84 stacks of the at least one voxel. In some embodiments, the one or more regions of the brain include, but not limited, an inferior frontal gyrus, a pars triangularis, a caudate, a superior temporal gyrus, a middle occipital gyrus, a parahippocampal, an anugular gyrus, a middle frontal gyrus, a supramarginal gyrus, an inferior temporal gyrus, a crus I of cerebellar hemisphere, a precentral gyrus, a precuneus, and a middle frontal gyrus.

The brain activity analyzing server 106 classifies the activity and the connectivity of the brain into at least one neuropsychiatric disorder based on a percentage of variation of intensity of the at least one voxel in the one or more regions of the brain over the one or more features from a predefined threshold value associated with a normal activity and connectivity of the brain. The brain activity analyzing server 106 generates a report that visualizes the percentage of deviation from the normal activity and connectivity of the brain. In some embodiments, the report includes at least one of a three dimensional or a four dimensional MRI image that visualizes the changes in the functional connectivity and the activity of the brain. In some embodiments, the report includes at least one of one or more accuracy matrices, one or more percentage matching graphs, or one or more scatter plots. In some embodiments, the percentage of deviation is visualized on a screen of the expert device 108. In some embodiments, the brain activity analyzing server 106 may generate a report including the classification of the brain activity and connectivity of the person.

Figure 2:
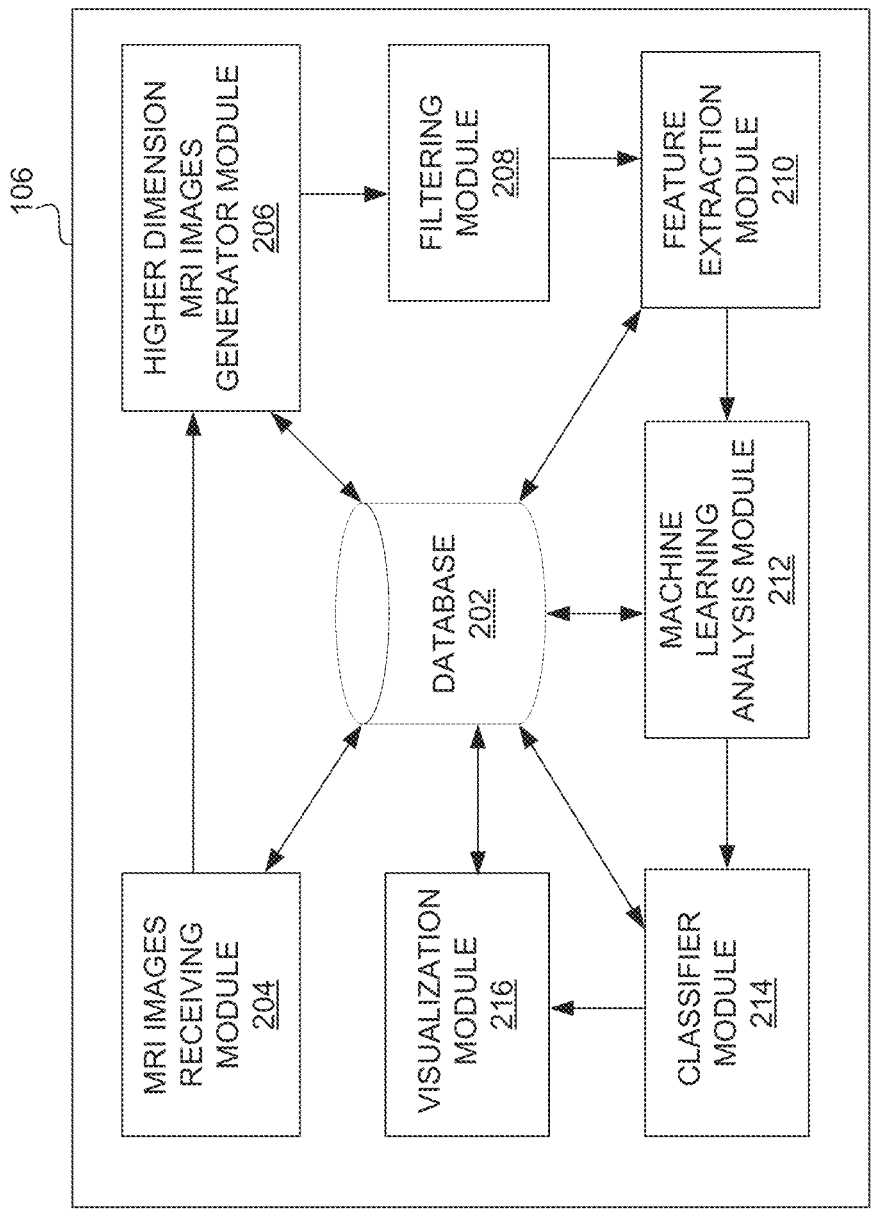
FIG. 2 illustrates an exploded view of a brain activity analyzing server, according to an embodiment herein.

FIG. 2 illustrates an exploded view of a brain activity analyzing server 106, according to an embodiment herein. The brain activity analyzing server 106 includes a database 202, a magnetic response imaging (MRI) image receiving module 204, a higher dimension MRI image generator module 206, a filtering module 208, a feature extraction module 210, a machine learning analysis module 212, a classifier module 214, and a visualization module 216. The MRI image receiving module 204 obtains one or more two-dimensional (2D) slices of structural MRI images and one or more two-dimensional (2D) slices of functional MRI images of the brain from the imaging device 102. The database 202 stores the received MRI images from the MRI image receiving module 204. In some embodiments, the 2D slices of structural MRI images and 2D slices of functional MRI images are stored in a dicom format. In some embodiments, the imaging device 102 may collect MRI image data of the person in the dicom format. In some embodiments, the MRI image data of the person includes a number of attributes, for example, a name of the person, an identification (ID) of the person, etc., a number of slices of the MRI images, a voxel size, and a number of functional MRI time-series points from a dicom header. In some embodiments, the received one or more 2D slices of structural MRI images of the brain, and the one or more 2D slices of functional MRI images overtime of the brain are pre-processed. In some embodiments, the pre-processing of one or more 2D slices of structural MRI image of the brain, and the 2D slices of the functional MRI image includes (i) setting an origin of the one or more 2D slices of structural MRI images of the brain, and the one or more 2D slices of the functional MRI images of the brain based on an anterior commissure, and a posterior commisure lines, (ii) calculating resting state functional MRI metrics in a native space, (iii) removing the first 10 time points for scanner calibration, wherein the time point is the total time taken for a complete scan, (iv) correcting slice time by examining time shift by small amount for each voxel sampled across slices of the one or more 2D slices of structural MRI images of the brain, and the one or more 2D slices of the functional MRI images by interpolating between the time points of sampling to give the time course that is like having sampled each voxel at the same time, (v) realigning the one or more 2D slices of structural MRI image of the brain, and the one or more 2D slices of the functional MRI image to remove movement artefacts, and (vi) generating automasks in skull stripping of the one or more 2D slices of structural MRI images of the brain, and the one or more 2D slices of the functional MRI images. The higher dimension MRI image generator module 206 generates a 3D structural MRI image and 4D functional MRI image of the brain using an image processing technique. In some embodiments, the higher dimension MRI image generator module 206 segments the 3D structural MRI image and the 4D functional MRI image of the brain into one or more parts. In some embodiments, the higher dimension MRI image generator module 206, for example, segments 4D functional MRI image of the brain into gray matter, white matter, and cerebrospinal fluid. In some embodiments, the higher dimension MRI image generator module 206 regularizes the 3D structural MRI image and the 4D functional MRI image of the brain by penalizing excessive stretching or shrinking. In some embodiments, the higher dimension MRI image generator module 206 regresses out motion parameters and corrects the effects of motion by removing motion-related components from the 3D structural MRI image and the 4D functional MRI image of the brain by the inclusion of calculated motion parameters. In some embodiments, the higher dimension MRI image generator module 206 normalizes the motion artefacts regressed 3D structural MRI image and 4D functional MRI image of the brain. In some embodiments, the higher dimension MRI image generator module 206 smoothens the normalized 3D structural MRI image and 4D functional MRI image of the brain. In some embodiments, the higher dimension MRI image generator module 206 generates a default mask for the smoothened the normalized the 3D structural MRI image and 4D functional MRI image of the brain. The filtering module 208 filters higher frequency components in the 3D structural MRI image and 4D functional MRI image of the brain to obtain low frequency components using a bandpass filter. The feature extraction module 210 extracts one or more features associated with one or more regions of the brain in a co-registered MRI image of the brain. In some embodiments, the co-registered MRI image is created by co-registering the 3D structural MRI image to the 4D functional MRI image. In some embodiments, the co-registered MRI image is parcellated into the one or more regions of the brain using a parcellation scheme. In some embodiments, the one or more features of the brain includes, but not limited to, one or more derivatives of functional connectivity pearson correlation, a functional connectivity partial co-relation, a functional connectivity precision, an amplitude of low frequency fluctuation (ALFF), a fractional Amplitude of Low Frequency Fluctuations (fALFF), and a regional homogeneity. In some embodiments, the amplitude of low frequency fluctuation (ALFF), and the fractional Amplitude of Low Frequency Fluctuations (fALFF) are obtained in the form of nifty file intensity maps using the bandpass filter. The machine learning analysis module 212 analyses, using a machine learning model, an intensity of at least one voxel in the one or more regions of the brain over one or more features to determine an activity and a connectivity of the brain over the one or more features. In some embodiments, the machine learning analysis module 212 reduces the one or more features by checking the importance of the one or more features of the brain and contribution of the one or more features of the brain to analyse the one or more regions of the brain. In some embodiments, the one or more features of the brain are extracted using a standardized parcellations algorithm. In some embodiments, the machine learning analysis module 212 analyses, using a machine learning model on a single stack of at least one voxel. In some embodiments, the single stack includes any six of the extracted one or more features of the brain. In some embodiments, the machine learning model includes supervised learning algorithms and unsupervised learning algorithms. In some embodiments, the supervised learning algorithms include a decision tree learning, a linear model analysis, a support vector machine algorithm, graphical models, deep neural networks, an ensemble learning algorithm, classification models, and regression models. In some embodiments, the unsupervised learning algorithms include a clustering based algorithm, a graph based algorithm, a component-based learning algorithm, a hierarchical clustering based algorithm, and a mixture model. In some embodiments, the semi-supervised and reinforcement models are applied to the single stack. In some embodiments, the machine learning analysis module 212 analyses, using the machine learning model on a multi-stack of at least one voxel to obtain a classification of the activity and the connectivity of the brain into at least one neuropsychiatric disorder. In some embodiments, the multi-stack includes 84 stacks of at least one voxel. In some embodiments, the one or more regions of the brain include, but not limited, an inferior frontal gyrus, a pars triangularis, a caudate, a superior temporal gyrus, a middle occipital gyrus, a parahippocampal, an anugular gyrus, a middle frontal gyrus, a supramarginal gyrus, an inferior temporal gyrus, a crus I of cerebellar hemisphere, a precentral gyrus, a precuneus, and a middle frontal gyrus. The classifier module 214 classifies the activity and the connectivity of a brain into at least one neuropsychiatric disorder based on a percentage of variation of intensity of the at least one voxel in the one or more regions of the brain over the one or more features from a predefined threshold value associated with a normal activity of the brain. The visualization module 216 generates a report that visualizes the percentage of deviation from the normal activity of the brain. In some embodiments, the report includes at least one of a three dimensional or a four dimensional MRI image that visualizes the changes in the functional connectivity and the activity of the brain. In some embodiments, the report includes one or more accuracy matrices, one or more percentage matching graphs, and one or more scatter plots.

Figure 3:
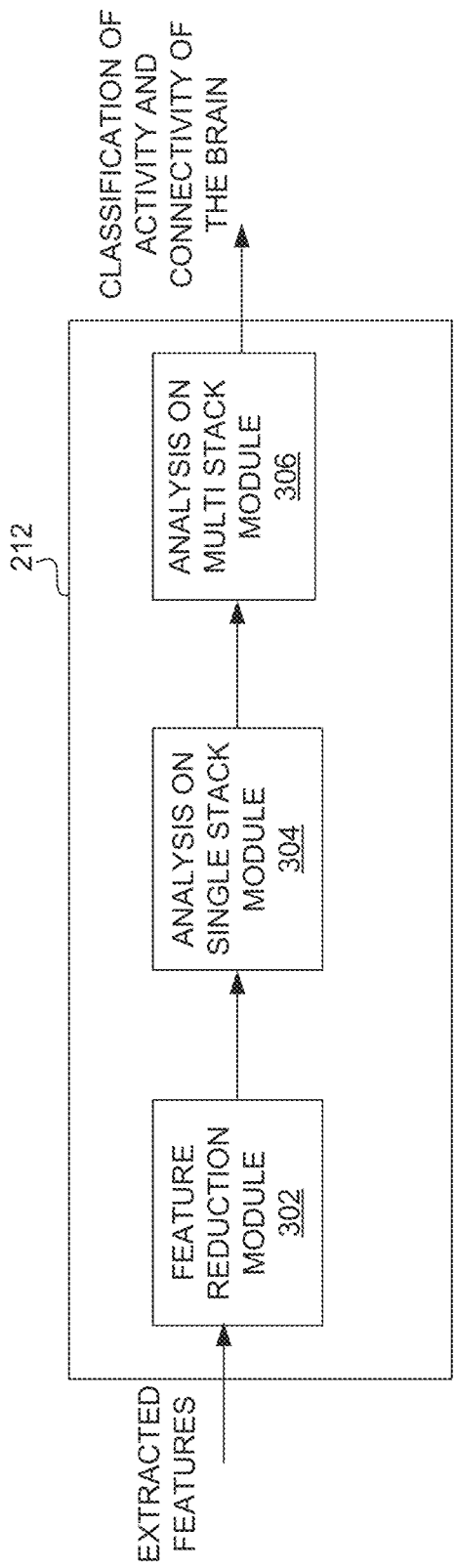
FIG. 3 illustrates an exploded view of a machine learning analysis module, according to an embodiment herein.

FIG. 3 illustrates an exploded view of the machine learning analysis module 212, according to an embodiment herein. The machine learning analysis module 212 includes a feature reduction module 302, an analysis on single-stack module 304, and an analysis on multi-stack module 306. The feature reduction module 302 reduces the one or more features by checking the importance of the one or more features of the brain and contribution of the one or more features of the brain to analyse the one or more regions of the brain. In some embodiments, the one or more features of the brain are extracted using a standardized parcellations algorithm. The analysis on single-stack module 304 analyses, using a machine learning model on a single stack of at least one voxel. In some embodiments, the single stack includes any six of the extracted one or more features of the brain. In some embodiments, the machine learning model includes supervised learning algorithms and unsupervised learning algorithms. In some embodiments, the supervised learning algorithms include decision tree learning, linear model analysis, a support vector machine algorithm, graphical models, deep neural networks, an ensemble learning algorithm, classification models, and regression models. In some embodiments, the unsupervised learning algorithms include a clustering based algorithm, graph based algorithm, and a component-based learning algorithm, a hierarchical clustering algorithm, and a mixture model. In some embodiments, semi-supervised and reinforcement models are applied to the single stack. In some embodiments, the single stack includes any six of the extracted one or more features of the brain. The analysis on multi-stack module 306 analyses, using the machine learning model on a multi-stack of at least one voxel to obtain a classification of the activity and the connectivity of the brain into at least one neuropsychiatric disorder. In some embodiments, the multi-stack includes 84 stacks of the at least one voxel. In some embodiments, the one or more regions of the brain are the inferior frontal gyrus, the pars triangularis, the caudate, the superior temporal gyrus, the middle occipital gyrus, the parahippocampal, the anugular gyrus, the middle frontal gyrus, the supramarginal gyrus, the inferior temporal gyrus, the crus I of cerebellar hemisphere, the precentral gyrus, the precuneus, and the middle frontal gyrus.

FIGS. 4A to FIG. 4H illustrate exemplary representations of analysis of various extracted features from the functional MRI image and the structural MRI image of the brain, according to an embodiment herein. The exemplary representation of FIG. 4A visualizes higher activity in the one or more regions of the brain in a first color 402 and lower activity in the one or more regions of the brain in a second color 404. The intensity values associated with the higher activity and the lower activity in the one or more regions of the brain are shown in the following table 1.

TABLE 1

| Regions of the brain | Peak intensity | Activity |
| --- | --- | --- |
| Inferior frontal gyms | 5.2 | Higher |
| Pars triangularis | 5.2 | Higher |
| Caudate | 5.5 | Higher |
| Superior temporal gyms | 4.7 | Higher |
| Middle occipital gyms | 5.1 | Higher |

TABLE 1-continued

| Regions of the brain | Peak intensity | Activity |
| --- | --- | --- |
| Para hippocampal | 3.8 | Higher |
| Angular gyms | 6.5 | Lower |
| Middle frontal gyms | 7.8 | Lower |
| Supra Marginal gyms | 4.7 | Lower |
| Inferior temporal gyms | 4.7 | Lower |
| Crus I of cerebellar hemisphere | 4.4 | Lower |
| Precentral gyms | 6 | Lower |
| Precuneus | 3.5 | Lower |
| Middle Frontal gyms | 5 | Lower |

Figure 4A:
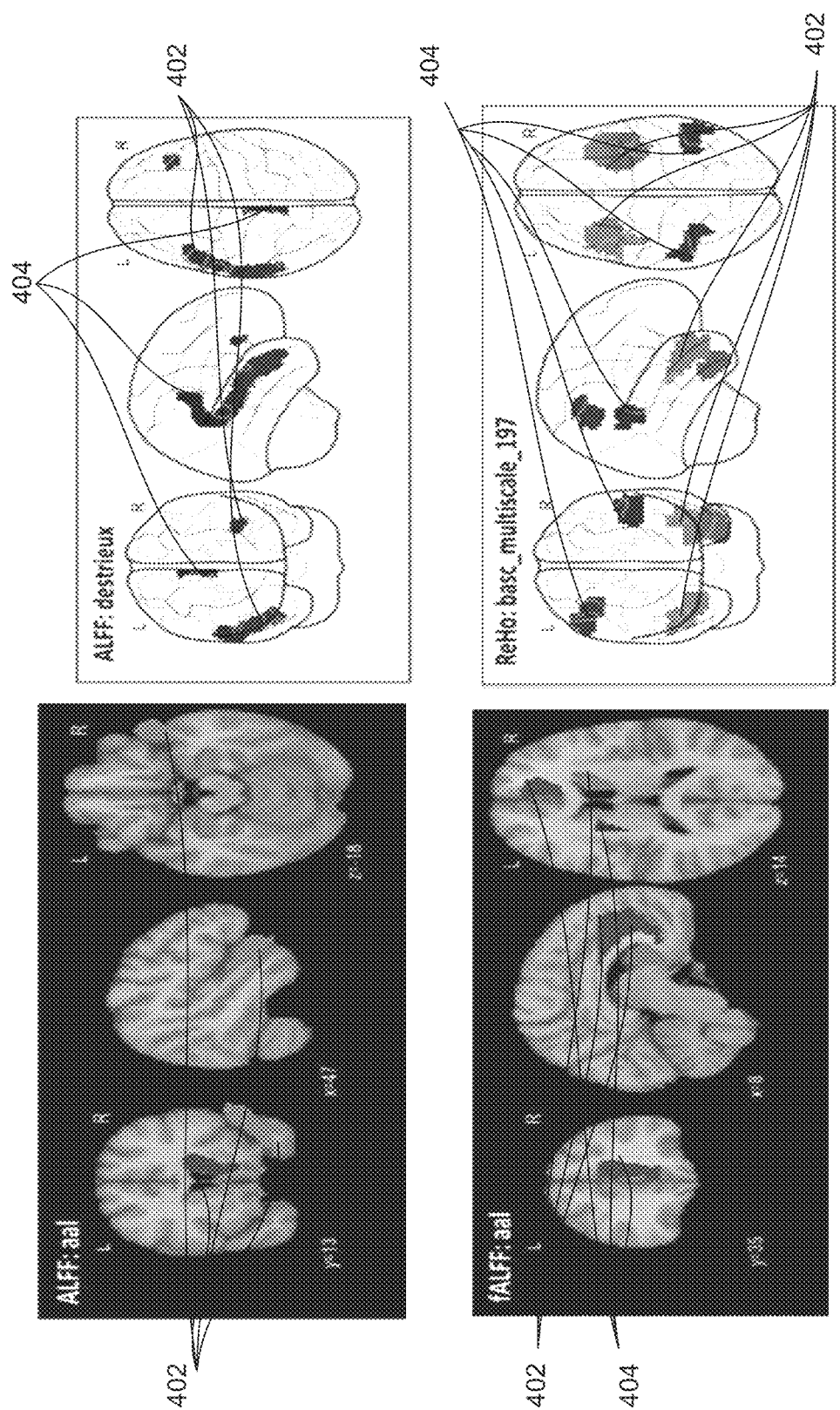
FIGS. 4A to 4H illustrate exemplary representations of analysis of various extracted features from the functional MRI image and the structural MRI image, according to an embodiment herein.
Figure 4B:
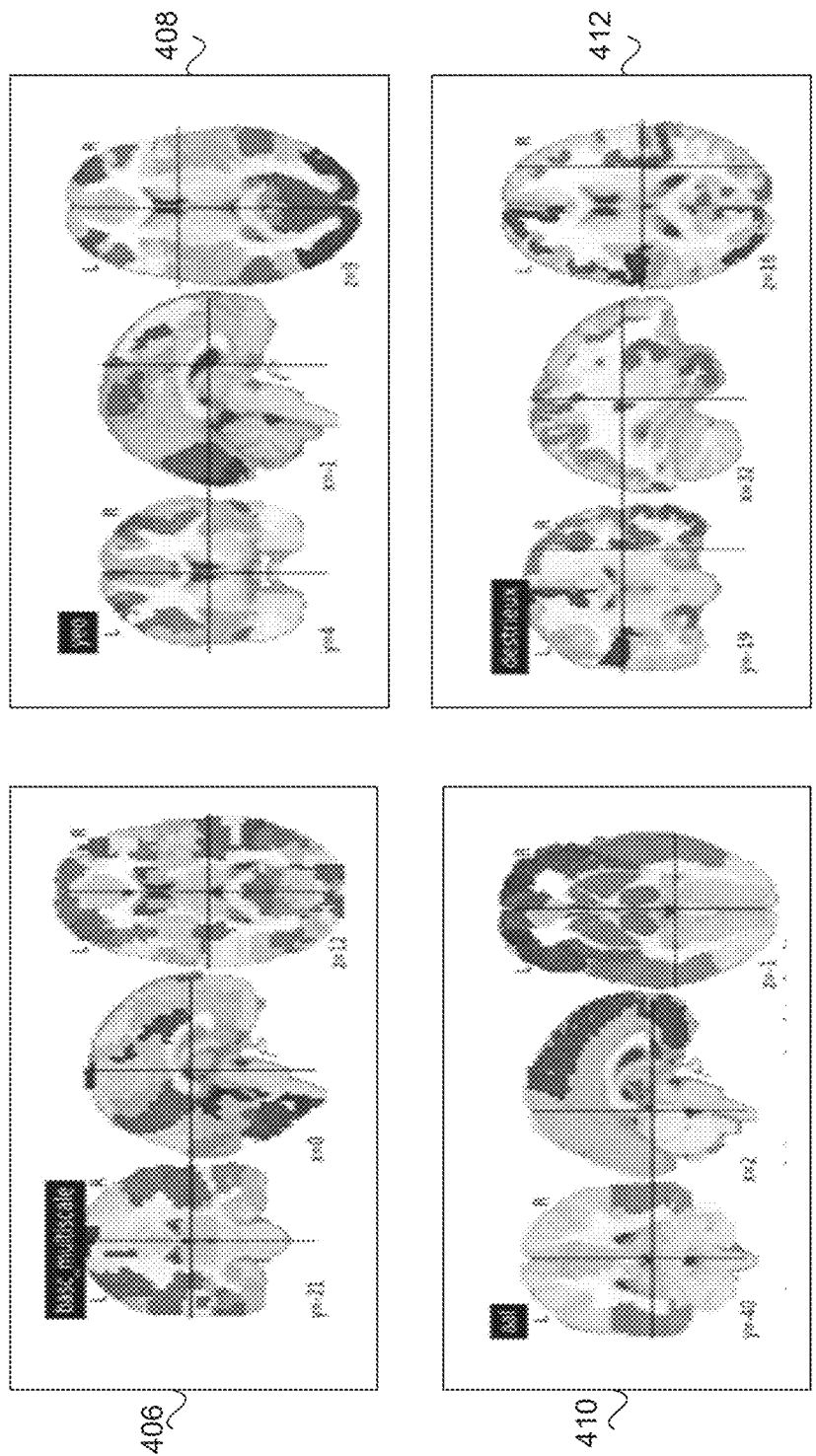
Figure 4C:
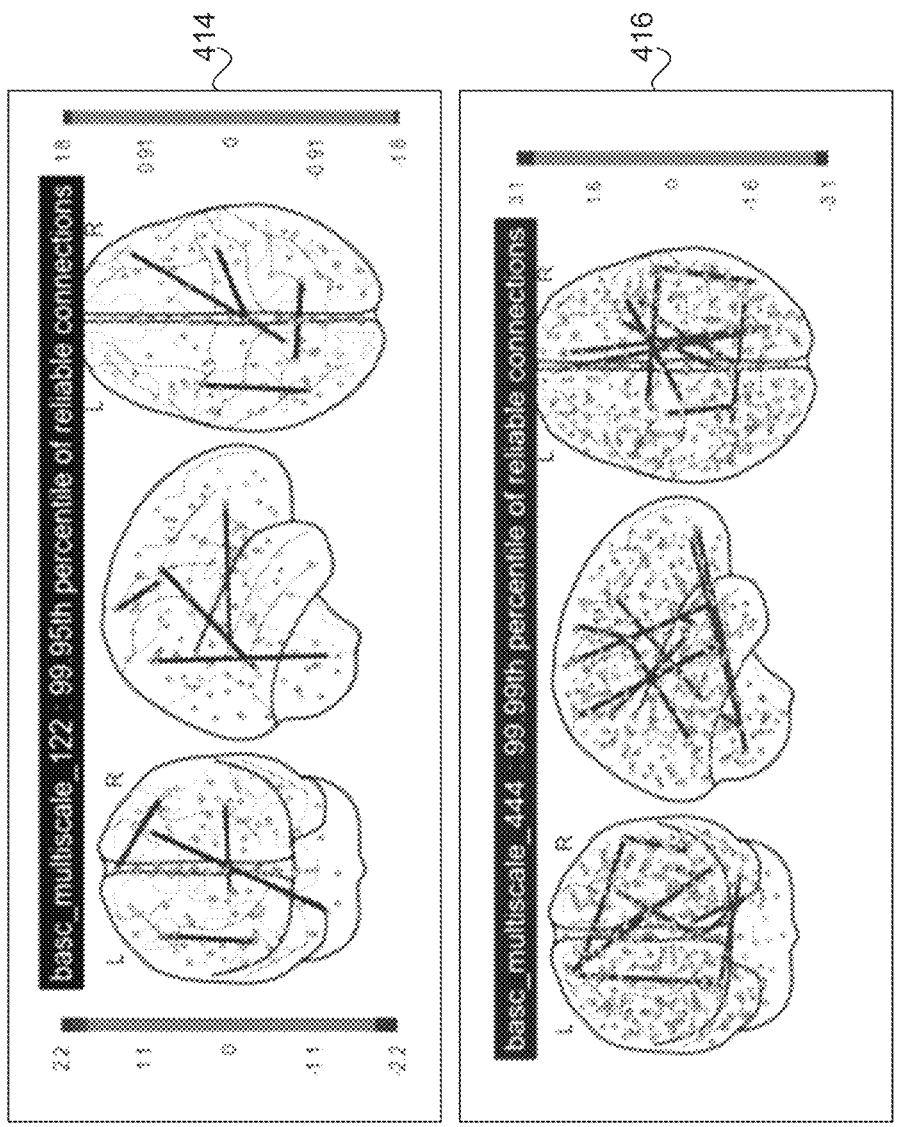
Figure 4E:
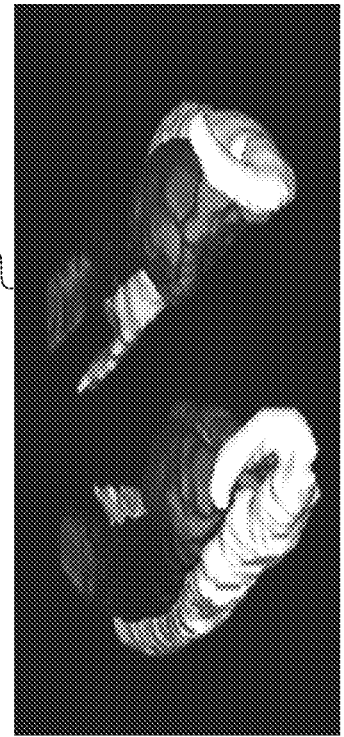
Figure 4F:
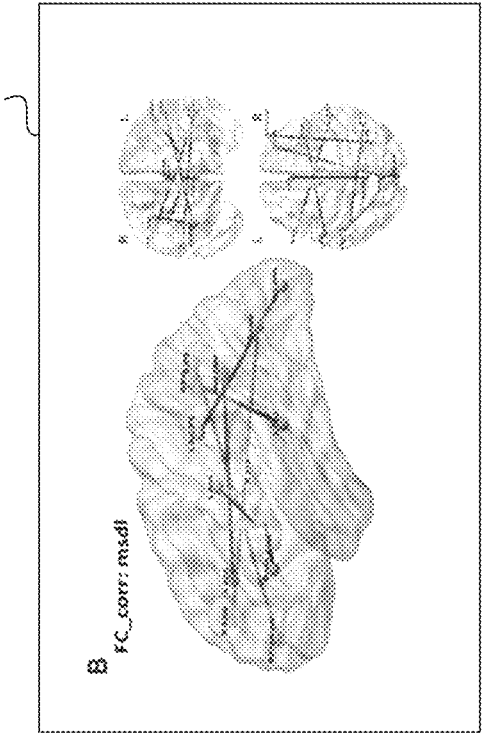
Figure 4D:
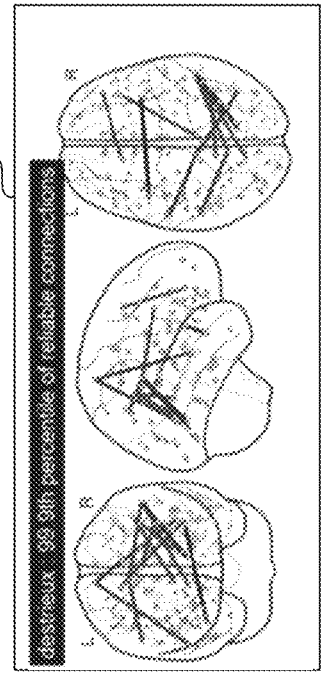

In some embodiments, the one or more regions of the brain shown in the first color include right caudate, right superior temporal pole, in the lateral aspect of left superior temporal gyrus, horizontal ramus of the right lateral sulcus, left putamen, right caudate and left superior temporal pole. In some embodiments, the one or more regions of the brain shown in the second color include left posterior-dorsal cingulate gyrus, right anterior cingulum, left inferior parietal lobule, and right superior temporal gyrus. The exemplary representation 406 in the FIG. 4B visualizes the multi-level analysis of stable clusters in the resting-state functional MRI. The exemplary representation 408 in the FIG. 4B visualizes intrinsic functional connectivity between the one or more regions of the brain. The exemplary representation 410 in the FIG. 4B visualizes automated anatomical labeling of the structural MRI image. The exemplary representation 412 in the FIG. 4B visualizes a sulcal depth-based anatomical division of the structural MRI image. The exemplary representation 414 in the FIG. 4C represents the analysis of stable clusters in resting-state functional MRI in a first resolution. The exemplary representation 416 in the FIG. 4C represents the analysis of stable clusters in resting-state functional MRI in a second resolution. The exemplary representation 418 of FIG. 4D visualizes the sulcal depth-based anatomical division of cerebral cortex. The exemplary representation 420 in the FIG. 4E visualizes the structural MRI of the person that provides volume analysis of the brain. In some embodiments, the volume analysis of the brain includes reduced grey matter volume and classifying the volume of the brain into Hippocampus, Pre-frontal cortex, anterior cingulate. The volume analysis of the person is represented in the following table 2.

TABLE 2

| Region of the brain | Difference from control group | Difference from average group |
| --- | --- | --- |
| Grey matter reduction | — | — |
| Hippocampus | 5% | — |
| Left Pre-frontal cortex | 8% | — |
| Right and left anterior cingulate | 12% | — |
| Caudate | 3% | 6% |

Figure 4H:
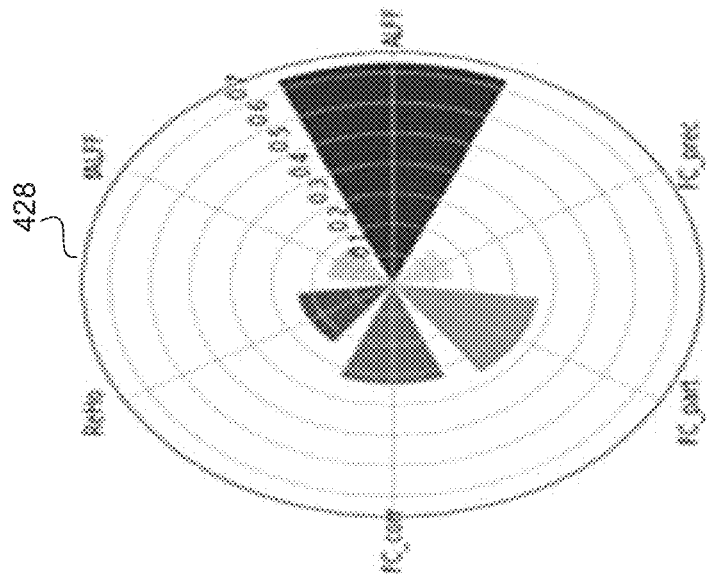
Figure 4G:
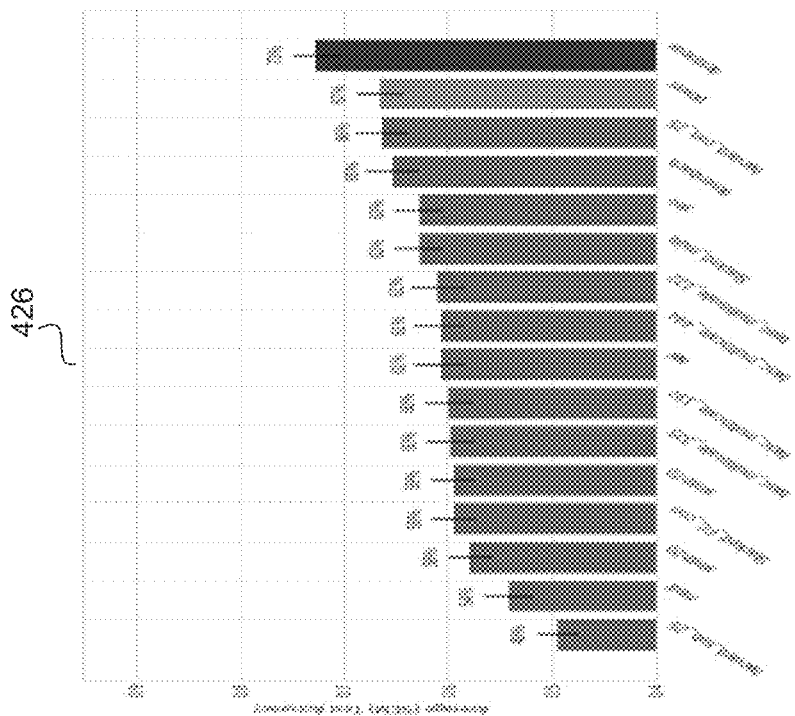

In some embodiments, the volume analysis of the brain is shown among differences from a control group and differences from an average group. The exemplary representations 422 and 424 in the FIG. 4F visualizes key pathological alterations associated with schizophrenia disorder that is classified by comparing features of the person with a set of predefined features. In some embodiments, the decreased functional connectivity between regions of the left ventral frontal cortex and left lateral cerebellum, left occipital and left angular gyrus, left middle insula and right fusiform gyrus, and lastly left post parietal, left precentral gyrus are identified in the exemplary representation 422. In some embodiments, increased inter-hemispheric functional connectivity between left superior frontal gyrus and the right anterior insula is identified in the exemplary representation 422. In some embodiments, the decreased functional connectivity between regions striatum and posterior occipital lobe, right intra-parietal sulcus and right frontal pole, ventral anterior cingulate cortex, and medial default mode network, left temporoparietal junction and right parietal cortex, right superior temporal sulcus and Broca' s area are identified in the exemplary representation 424. In some embodiments, the increased functional connectivity between regions that is right anterior insula and striatum, right insula and left auditory cortex, and left anterior intra-parietal sulcus and the posterior occipital lobe are identified in the exemplary representation 424. FIG. 4G shows the exemplary representation of a graph 426 that shows the accuracy of the classification of schizophrenia and bipolar disorder. In some embodiments, the graph 426 shows comparison across one or more divisions at X-axis and stacked predictions at Y-axis. FIG. 4H shows an exemplary representation of a graphical representation 428 of the percentage of deviation of the activity of the person who has been tested from the normal activity of the brain of the person in the one or more regions of the brain.

Figure 5:
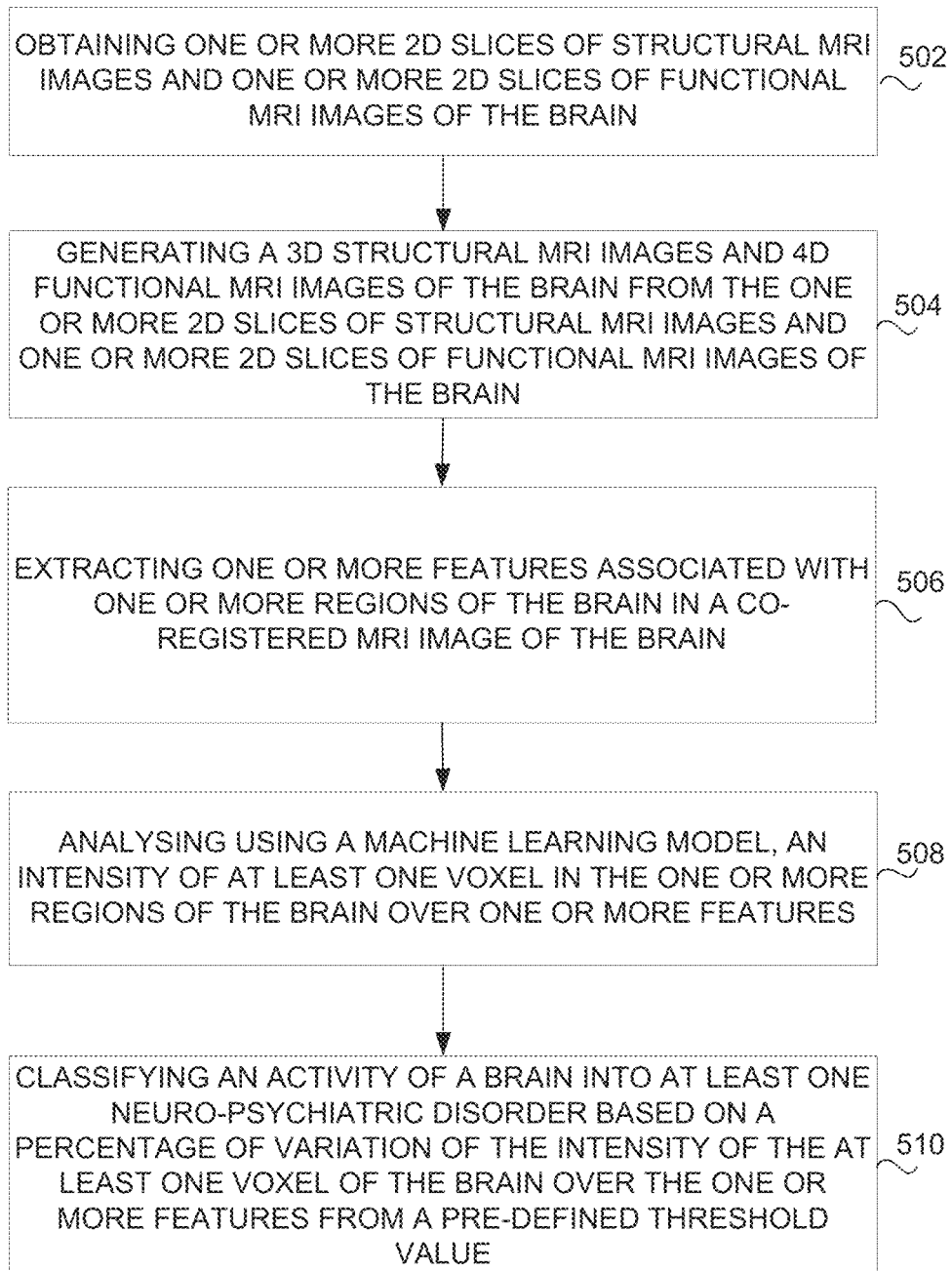
FIG. 5 is a flow diagram that illustrates a method for classifying an activity and a connectivity of a brain into at least one neuro-psychiatric disorder from magnetic resonance imaging (MRI) images, according to an embodiment herein.

FIG. 5 is a flow diagram that illustrates a method 500 for classifying an activity and a connectivity of a brain into at least one neuro-psychiatric disorder from magnetic resonance imaging (MRI) images, according to an embodiment herein. At step 502, the method 500 includes the step of obtaining one or more two-dimensional slices of structural MRI images and one or more two-dimensional slices of functional MRI images of a brain. At step 504, the method 500 includes the step of generating a three-dimensional structural MRI image and a four-dimensional functional MRI image of the brain from the one or more two-dimensional slices of structural MRI images and the one or more two-dimensional slices of functional MRI images of the brain. At step 506, the method 500 includes the step of extracting one or more features associated with one or more regions of the brain in a co-registered MRI image of the brain. In some embodiments, the co-registered MRI image is created by co-registering the three-dimensional structural MRI image to the four-dimensional functional MRI image. In some embodiments, the co-registered MRI image is parcellated into the one or more regions of the brain using a parcellation scheme. At step 508, the method 500 includes the step of analyzing, using a machine learning model, an intensity of at least one voxel in the one or more regions of the brain over one or more features to determine the activity and the connectivity of the brain over the one or more features. At step 510, the method 500 includes the step of classifying the activity and the connectivity of a brain into at least one neuropsychiatric disorder based on a percentage of variation of intensity of the at least one voxel in the one or more regions of the brain over the one or more features deviates from a predefined threshold value.

Figure 6:
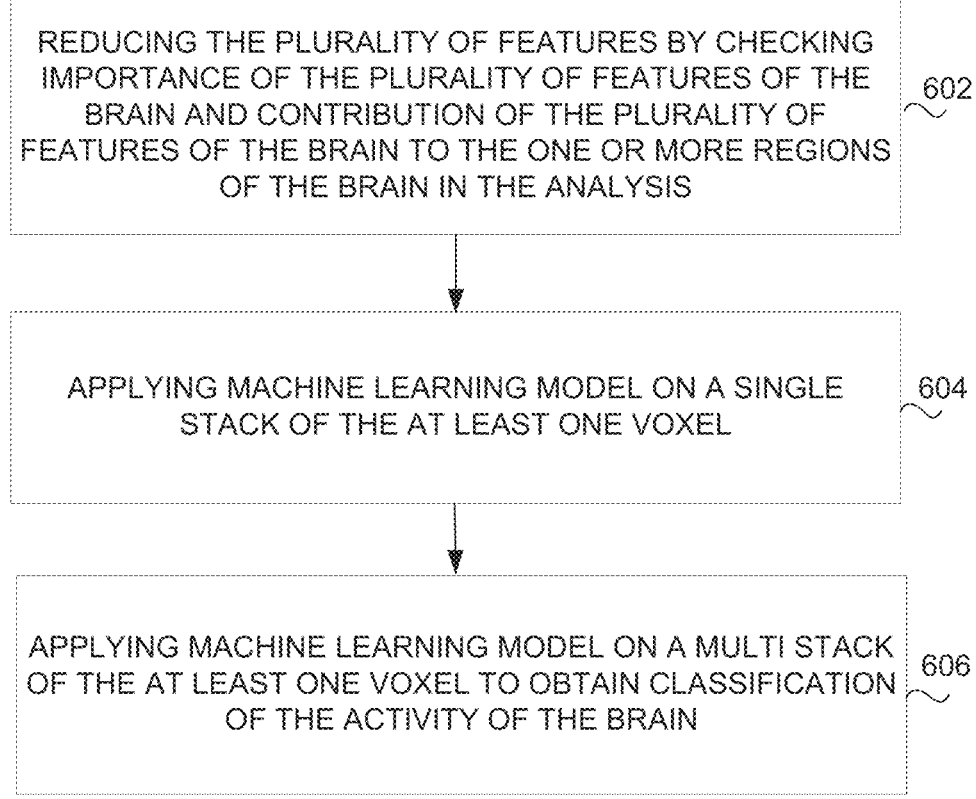
FIG. 6 is a flow diagram that illustrates a method of analysis of the activity of the brain, according to an embodiment herein.

FIG. 6 is a flow diagram that illustrates a method 600 of analysis of the activity of the brain, according to an embodiment herein. At step 602, the method 600 includes the step of reducing the one or more features based on an importance and a contribution of the one or more features of the brain to analyse the one or more regions of the brain. At step 604, the method 600 includes the step of applying machine learning model on a single stack of the at least one voxel. In some embodiments, the single stack includes any six of the extracted one or more features of the brain. At step 606, the method 600 includes the step of applying machine learning model on a multi-stack of the at least one voxel to obtain classification of the activity and the connectivity of the brain, the multi-stack comprises 84 stacks.

Figure 7:
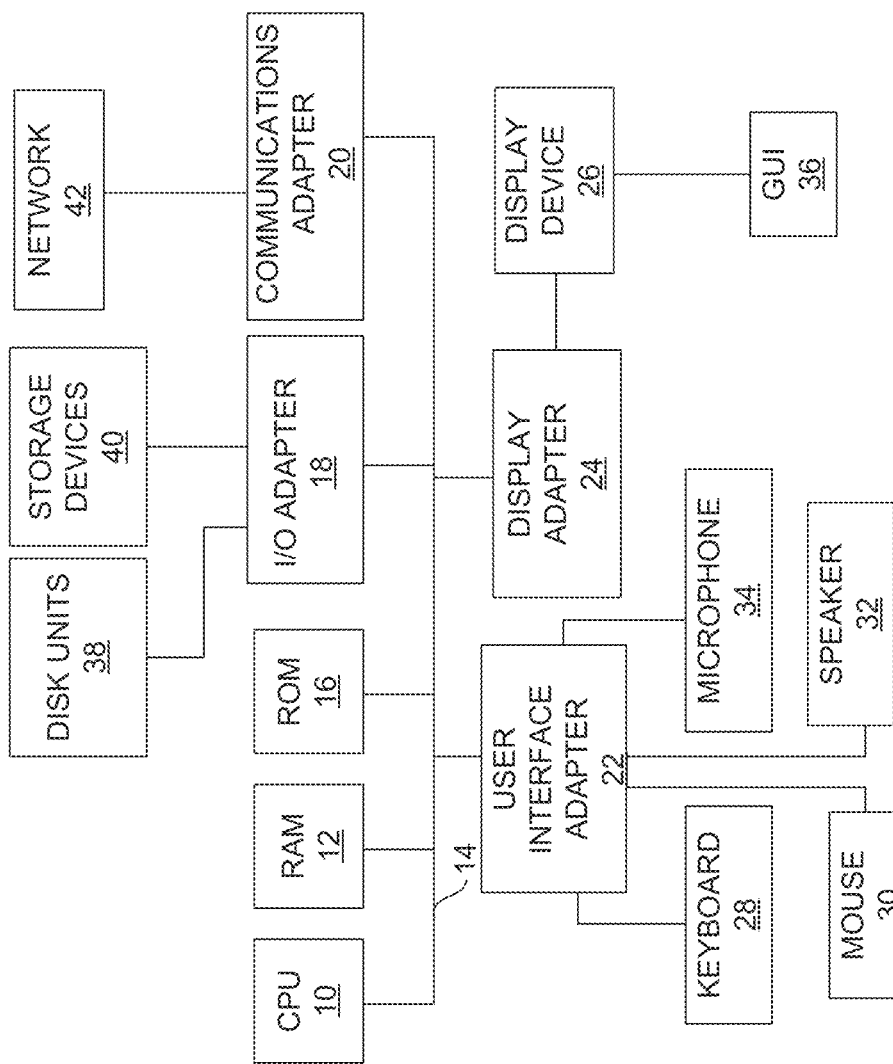
FIG. 7 is a schematic diagram of a computer architecture of a brain activity analyzing server, in accordance with the embodiments herein.

A representative hardware environment for practicing the embodiments herein is depicted in FIG. 7, with reference to FIGS. 1 through 6. This schematic drawing illustrates a hardware configuration of a brain activity analyzing server 106/computer system/computing device in accordance with the embodiments herein. The system includes at least one processing device CPU 10 that may be interconnected via system bus 15 to various devices such as a random access memory (RAM) 12, read-only memory (ROM) 16, and an input/output (I/O) adapter 18. The I/O adapter 18 can connect to peripheral devices, such as disk units 58 and program storage devices 50 that are readable by the system. The system can read the inventive instructions on the program storage devices 50 and follow these instructions to execute the methodology of the embodiments herein. The system further includes a user interface adapter 22 that connects a keyboard 28, mouse 50, speaker 52, microphone 55, and/or other user interface devices such as a touch screen device (not shown) to the bus 15 to gather user input. Additionally, a communication adapter 20 connects the bus 15 to a data processing network 52, and a display adapter 25 connects the bus 15 to a display device 26, which provides a graphical user interface (GUI) 56 of the output data in accordance with the embodiments herein, or which may be embodied as an output device such as a monitor, printer, or transmitter, for example.

The system and/or method is used for generating suggestions to healthcare experts related to psychiatric, neuropsychiatric, neurodevelopmental, neurological, neuro-sensory disorders using functional MRI and structural MRI of a patient. The system or method may help the experts in performing very fast analysis, diagnostic assistance, and reports within a day. This system is mostly helpful for psychiatrists, neurologists, radiologists. The system or method may help in promoting various types of brain activity for disease diagnosis and studying complex diseases like schizophrenia, schizo-affective, bipolar, several dementia disorders, and psychotic depression. Also, the system or method may beneficial to understand the brain structure or activity for determining abnormity and potential pathogenesis of the diseases.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A processor-implemented method for classifying an activity and connectivity of a brain into at least one neuro-psychiatric disorder from magnetic resonance imaging (MRI) images, wherein the method comprising:

obtaining a plurality of two-dimensional slices of structural MRI images and a plurality of two-dimensional slices of functional MRI images of the brain;

generating a three-dimensional structural MRI image and a four-dimensional functional MRI image of the brain from the plurality of two-dimensional slices of structural MRI images and the plurality of two-dimensional slices of functional MRI images of the brain;

extracting a plurality of features associated with a plurality of regions of the brain in a co-registered MRI image of the brain, wherein the co-registered MRI image is created by co-registering the three-dimensional structural MRI image to the four-dimensional functional MRI image, wherein the co-registered MRI image is parcellated into the plurality of regions of the brain using a parcellation scheme;

analysing, using a machine learning model, an intensity of at least one voxel in the plurality of regions of the brain over a plurality of features to determine an activity and a connectivity of the brain over the plurality of features; and classifying the activity and the connectivity of the brain into at least one neuropsychiatric disorder based on a percentage of variation of the intensity of the at least one voxel over the plurality of features from a predefined threshold value.

2. The method of claim 1, wherein the plurality of regions of the brain comprises at least one of an inferior frontal gyrus, a pars triangularis, a caudate, a superior temporal gyrus, a middle occipital gyrus, a parahippocampal, an anugular gyrus, a middle frontal gyrus, a supramarginal gyrus, an inferior temporal gyrus, a crus I of cerebellar hemisphere, a precentral gyrus, a precuneus, or a middle frontal gyrus.

3. The method of claim 1, wherein the plurality of features of the brain comprises at least one of a regional homogeneity, a plurality of derivatives of functional connectivity pearson correlation, a functional connectivity partial co-relation, a functional connectivity precision, an amplitude of low frequency fluctuation (ALFF), or a fractional Amplitude of Low Frequency Fluctuations (fALFF).

4. The method of claim 3, wherein the method comprises calculating the functional connectivity between the plurality of regions of the brain using an intensity of the at least one voxel and a plurality of activation time series components of the at least one voxel.

5. The method of claim 3, wherein the method comprises calculating the amplitude of low frequency fluctuation (ALFF), and the fractional Amplitude of Low Frequency Fluctuations (fALFF) in the form of nifty file intensity maps using a bandpass filter.

6. The method of claim 1, wherein the method comprises generating a report that visualizes percentage of deviation of the activity and the connectivity of the brain over the plurality of features from the normal activity and connectivity of the brain, wherein the report comprises at least one of a plurality of accuracy matrices, a plurality of percentage matching graphs, or a plurality of scatter plots.

7. The method of claim 1, wherein the method comprises analysing of the intensity of the at least one voxel in the plurality of regions of the brain over the plurality of features by, reducing the plurality of features based on an importance and a contribution of the plurality of features of the brain to analyse the plurality of regions of the brain;

analysing, using the machine learning model, on a single stack of the at least one voxel, wherein the single stack comprises any six of the extracted plurality of features of the brain; and analysing, using the machine learning model, on a multi stack of the at least one voxel to obtain classification of the activity and the connectivity of the brain, wherein the multi stack comprises 84 stacks of the at least one voxel.

8. The method of claim 7, wherein the machine learning model comprises supervised learning algorithms and unsupervised learning algorithms, wherein the supervised learning algorithms comprise at least one of a decision tree learning algorithm, a linear model analysis algorithm, a support vector machine learning algorithm, graphical models, deep neural networks, or an ensemble learning algorithm.

9. The method of claim 7, wherein the unsupervised learning algorithms comprise at least one of a clustering model, a graph algorithm model, a component based model, a hierarchical clustering algorithm, or a mixture model learning.

10. The method of claim 1, wherein the method comprises pre-processing the two-dimensional structural MRI image slices of the brain and the two dimensional functional MRI image slices over time of the brain for feature extraction.

11. One or more non-transitory computer-readable storage medium storing the one or more sequence of instructions for classifying an activity and a connectivity of a brain into at least one neuropsychiatric disorder from magnetic resonance imaging (MRI) images which when executed by a processor causes:

obtaining a plurality of two-dimensional slices of structural MRI images and a plurality of two-dimensional slices of functional MRI images of the brain;

generating a three-dimensional structural MRI image and a four-dimensional functional MRI image of the brain from the plurality of two-dimensional slices of structural MRI images and the plurality of two-dimensional slices of functional MRI images of the brain;

extracting a plurality of features associated with a plurality of regions of the brain in a co-registered MRI image of the brain, wherein the co-registered MRI image is created by co-registering the three-dimensional structural MRI image to the four-dimensional functional MRI image, wherein the co-registered MRI image is parcellated into the plurality of regions of the brain using a parcellation scheme;

analysing, using a machine learning model, an intensity of at least one voxel in the plurality of regions of the brain over a plurality of features to determine an activity and a connectivity of the brain over the plurality of features; and classifying the activity and the connectivity of the brain into at least one neuropsychiatric disorder based on a percentage of variation of the intensity of the at least one voxel over the plurality of features from a predefined threshold value.

12. A system of classifying an activity and a connectivity of a brain of a user into at least one neuropsychiatric disorder from magnetic resonance imaging (MRI) images, the system comprising:

a processor; and a memory that stores a set of instructions which when executed by the processor performs obtaining a plurality of two-dimensional slices of structural MRI images and a plurality of two-dimensional slices of functional MRI images of the brain;

generating a three-dimensional structural MRI image and a four-dimensional functional MRI image of the brain from the plurality of two-dimensional slices of structural MRI images and the plurality of two-dimensional slices of functional MRI images of the brain;

extracting a plurality of features associated with a plurality of regions of the brain in a co-registered MRI image of the brain, wherein the co-registered MRI image is created by co-registering the three-dimensional structural MRI image to the four-dimensional functional MRI image, wherein the co-registered MRI image is parcellated into the plurality of regions of the brain using a parcellation scheme;

analysing, using a machine learning model, an intensity of at least one voxel in the plurality of regions of the brain over a plurality of features to determine an activity and a connectivity of the brain over the plurality of features; and classifying the activity and a connectivity of the brain into at least one neuropsychiatric disorder based on a percentage of variation of the intensity of the at least one voxel over the plurality of features from a predefined threshold value.

13. The system of claim 12, wherein the processor performs analysis of the intensity of the at least one voxel in the plurality of regions of the brain over the plurality of features by, reducing the plurality of features based on an importance and a contribution of the plurality of features of the brain to analyse the plurality of regions of the brain;

analysing, using the machine learning model, on a single stack of the at least one voxel, wherein the single stack comprises any six of the extracted plurality of features of the brain; and analysing, using the machine learning model, on a multi stack of the at least one voxel to obtain classification of the activity and the connectivity of the brain, wherein the multi stack comprises 84 stacks of the at least one voxel.

14. The system of claim 12, wherein the processor performs pre-processing the two-dimensional structural MRI image slices of the brain and the two dimensional functional MRI image slices over time of the brain for feature extraction.

15. The system of claim 13, wherein the machine learning model comprises supervised learning algorithms and unsupervised learning algorithms, wherein the supervised learning algorithms comprise at least one of a decision tree learning, a linear model analysis algorithm, a support vector machine algorithm, graphical models, deep neural networks, or an ensemble learning algorithm.

16. The system of claim 13, wherein the unsupervised learning algorithms comprise at least one of a clustering model, a graph algorithm model, a component-based model, a hierarchical clustering algorithm, or a mixture model learning.

17. The system of claim 12, wherein the plurality of regions of the brain comprises at least one of an inferior frontal gyrus, a pars triangularis, a caudate, a superior temporal gyrus, a middle occipital gyrus, a parahippocampal, an angular gyrus, a middle frontal gyrus, a supramarginal gyrus, an inferior temporal gyrus, a crus I of cerebellar hemisphere, a precentral gyrus, a precuneus, or a middle frontal gyrus.

18. The system of claim 12, wherein the plurality of features of the brain comprises at least one of a regional homogeneity, a plurality of derivatives of functional connectivity pearson correlation, a functional connectivity partial co-relation, a functional connectivity precision, an amplitude of low frequency fluctuation (ALFF), or a fractional Amplitude of Low Frequency Fluctuations (fALFF).

19. The system of claim 12, wherein the processor calculates the functional connectivity between the plurality of regions of the brain using an intensity of the at least one voxel and a plurality of activation time series components of the at least one voxel.

20. The system of claim 12, wherein the processor calculates the amplitude of low frequency fluctuation (ALFF), and the fractional Amplitude of Low Frequency Fluctuations (fALFF) are obtained in the form of nifty file intensity maps using a bandpass filter.

* * * * *